(12) United States Patent
Simanovsky et al.

(10) Patent No.: US 6,471,400 B1
(45) Date of Patent: Oct. 29, 2002

(54) ADAPTIVE CT MONITOR CORRECTION SYSTEM AND METHOD

(75) Inventors: Sergey Simanovsky, Brookline, MA (US); Carl R. Crawford, Brookline, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/016,570

(22) Filed: Oct. 26, 2001

Related U.S. Application Data

(60) Provisional application No. 60/243,651, filed on Oct. 26, 2000.

(51) Int. Cl.[7] .............................................. G01D 18/00
(52) U.S. Cl. ............................ 378/207; 378/4; 378/19; 378/20
(58) Field of Search .............................. 378/4, 19, 20, 378/207

(56) References Cited

U.S. PATENT DOCUMENTS

| | | | | |
|---|---|---|---|---|
| 4,769,827 A | | 9/1988 | Uno et al. ..................... 378/19 |
| 5,680,427 A | | 10/1997 | Dobbs et al. ................. 378/19 |
| 6,108,396 A | * | 8/2000 | Bechwati et al. ............. 378/15 |
| 6,128,365 A | * | 10/2000 | Bechwati et al. ............. 378/57 |
| 6,272,230 B1 | * | 8/2001 | Hiraoglu et al. ....... 250/363.04 |
| 6,317,509 B1 | * | 11/2001 | Simanovsky et al. .. 250/363.04 |

* cited by examiner

Primary Examiner—David P. Porta
Assistant Examiner—Pamela R. Hobden
(74) Attorney, Agent, or Firm—McDermott, Will & Emery

(57) ABSTRACT

Monitor detectors can be obstructed by the patient and/or the table, leading to image artifacts in a CT scanner. An algorithm for adaptive monitor correction is therefore provided, in which the algorithm replaces obstructed monitor readings with a value consistent with unobstructed monitor readings for the scan.

19 Claims, 6 Drawing Sheets

ADAPTIVE CT MONITOR CORRECTION SYSTEM AND METHOD

RELATED APPLICATION

This application is related to U.S. Provisional Patent Application Serial No. 60/243,651 filed on Oct. 26, 2000 in the name of Sergey Simanovsky, and assigned to the present assignee.

FIELD OF THE INVENTION

This invention relates generally to improving the quality of X-ray images, such as computed tomographic (CT) images, and more particularly to an improved system for and method of using readings of X-ray exposure taken during a CT scan to normalize image data derived from that scan.

BACKGROUND OF THE INVENTION

CT scanners of the third generation type include an X-ray source and X-ray detector system secured respectively on diametrically opposite sides of an annular-shaped disk. The latter is rotatably mounted within a gantry support so that during a scan the disk continuously rotates about a rotation axis while X-rays pass from the source through an object positioned within the opening of the disk to the detector system.

The detector system typically includes an array of detectors disposed in the shape of an arc of a circle having a center of curvature at the point, referred to as the "focal spot," where the radiation emanates from the X-ray source. The X-rays that are detected by a single detector at a measuring instant during a scan is considered a "ray." The ray is partially attenuated by all the mass in its path so as to generate a single intensity measurement as a function of the attenuation, and thus the density of the mass in that path. The X-ray source and array of detectors are all positioned so that the X-ray paths between the source and each detector define a "ray path". Because the ray paths originate from substantially a point source and extend at different angles to the detectors, the ray paths resemble a fan in the case of a single row of detectors, or a cone in the case of multiple rows of detectors. Projections or views, i.e., the X-ray intensity measurements, are typically done at each of a plurality of angular positions of the disk. The data can be acquired with the scanned object still, as for example, with a constant axis scan, or while the object and rotating disk are moved relative to one another in the direction of the Z-axis (the axis of rotation of the disk carrying the x-ray source and detector array) while the source and detector array rotate about the object, as for example, with a helical scan. The detector array can be symmetrical or asymmetrical about a ray passing from the source through the isocenter of the machine, i.e., the center of rotation of the X-ray source and detectors.

An image reconstructed from data acquired at all of the projection angles during the scan will be a slice made up of data acquired along the scanning section through the object being scanned. In the case of a constant axis scan the slice will be a plane passing through the Z-axis, while in the case of a helical scan the slice will be a volume portion of the object through which rays pass as the object is moved in the Z-axis direction. In order to "reconstruct" a density image of the section or "slice" of the object within the "field of view" in the defined scanning plane, the image is typically reconstructed in a pixel array, wherein each pixel in the array is attributed a value representative of the attenuation of all of the rays that pass through its corresponding position in the scanning plane during a scan. As the source and detectors rotate around the object, rays penetrate the object from different directions, or projection angles, passing through different combinations of pixel locations. The density distribution of the object in the slice section is mathematically generated from these measurements, and the brightness value of each pixel is set to represent that distribution. The result is an array of pixels of differing values which represents a density image of the slice plane.

As described in U.S. Pat. No. 5,680,427 (hereinafter the '427 Patent), issued to John M. Dobbs et al. and assigned to the present assignee, in order to produce a good quality image, the CT scanner designer works hard to minimize sources of error. Accordingly, steps are usually taken to provide for correction of errors either through design or calibration. For example, at zero X-ray levels it is important to minimize and stabilize signal offsets so that any measurement will contain a known constant offset for which corrections can be made. In addition, X-rays are provided at full scale and measurements are taken so as to generate "air" data with no absorbent material in the path of the X-rays so as to minimize errors due to drift in gain and measurement uncertainty at full scale. Two points of reference are thus provided between which data is corrected. In between these two points representing zero and full scale there is a curve which represents the relationship between X-ray levels and data values. The non-linear relationship between X-ray levels and data values results because the electrical signal varies in a non-linear manner with signal strength. Accordingly, materials of known absorption values (e.g., water, polyethylene, polyvinyl chloride, etc.) of predetermined thicknesses are placed within the path of the fan beam and data are generated in order to calibrate the system. The data will represent points on the curve. Using these known materials allows for the determination of the correct dosage level for a particular scan, and detector efficiency. A best fit polynomial can be easily determined using known techniques so that a look up table can be generated and stored.

Within the context of insuring good tomographic images, it is also important that the data represent identical detection for all of the detectors for any given number of photons. If one datum, representative of a number of photons received during the measurement period from one detector is different from the data received from all of the other channels for the same measurement, the result will be an artifact in the reconstructed image. Thus, steps have been taken in the past to calibrate the offset and gain of each data channel so that errors attributed to these two factors are minimized.

Additional errors are attributable to the source of X-rays. Even though an X-ray tube is set to provide a constant X-ray flux output, the number of photons striking the detectors within a prescribed period of time can vary from detector to detector. As mentioned above, it is also known that each photon contributes to noise. Thus, the fewer number of photons detected, the poorer the signal-to-noise ratio (S/N).

In addition, the X-ray source may fluctuate during the scan, particularly as it reaches the end of its "life", producing fluctuating intensities of the X-rays; and in at least one case even though the X-ray source is set to provide a given number of photons for each view, the signal can be degraded.

Typically, in order to account for fluctuating intensities of the X-rays, the CT data is normalized. More particularly, one of the first steps of a CT reconstruction algorithm is to calculate how much the X-rays are attenuated by the scanned object. This is accomplished by dividing the signal measured without an object in the X-ray path (called air scan) by the signal measured while scanning the object. A monitor (also called reference) detector is usually located so that the X-rays always pass from the source to the monitor detector without being attenuated by an object. The monitor data is used to account for fluctuations in the incident X-ray intensity during the air scan and the object scan. If a monitor detector is obstructed, the monitor data no longer reflects the incident X-ray intensity, which can lead to image artifacts.

Thus, it is known to utilize a monitor detector system to monitor the level of x-rays emitted by the X-ray source during a scan, and to use the monitor values to normalize the CT data taken at that time. The monitor detector system can be separate from the arcuate image detector array and positioned so that it remains clear of the object being scanned. See, for example, the '427 Patent. In some cases, where it may be desirable to eliminate a separate monitor detector system, because of the added costs it provides, detectors of the detector array can be used to acquire monitored data. For example, U.S. Pat. No. 4,769,827 issued Sep. 6, 1988 to Uno, et al., (the '827 Patent") provides a pair of reference detectors respectively at opposite ends of the arcuate image detector array to provide reference signals by which the data signals provided during a view can be compared, i.e., normalized. In one commercially available CT scan system, two detectors at the asymmetric end of the detector array are used as reference detectors, and obviously, the two end detectors of the symmetric end could be used. The problem with using detectors of the arcuate image detector array can be that during a scan, the rays from the X-ray source to the reference detectors is partially attenuated by the support table and object being scanned for certain positions of the gantry. As a result, monitor readings for those obstructed views are not valid for reference correction. In one prior art approach the reconstruction algorithm which uses the scanned data to reconstruct an image of the slice taken, uses an airtable-based threshold to replace low monitor readings. Thresholding obstructed monitor readings still leads to image artifacts because the monitor value is clipped at a value which is below the typical range for the scan.

SUMMARY OF THE INVENTION

An improved method of and system for correcting for X-ray fluctuations is provided. The adaptive monitor correction method and system uses all monitor readings for a scan to find views where monitor detectors are obstructed. Reference readings for obstructed views are replaced with one or more values calculated based on the remaining valid monitor readings. The values for the obstructed views are preferably statistically determined.

In one preferred embodiment a histogram of input monitor values and low-pass filtered monitor data are used in finding obstructed monitor views. Parameters controlling the algorithm performance were chosen after testing on several sets of raw data collected on the scanner. Monitor-related image artifacts are reduced by the adaptive monitor correction algorithm described hereinafter.

BRIEF DESCRIPTION OF THE DRAWINGS

The invention will be more fully understood from the following detailed description, in conjunction with the accompanying figures, wherein.

DETAILED DESCRIPTION OF THE DRAWINGS

Figure 1:
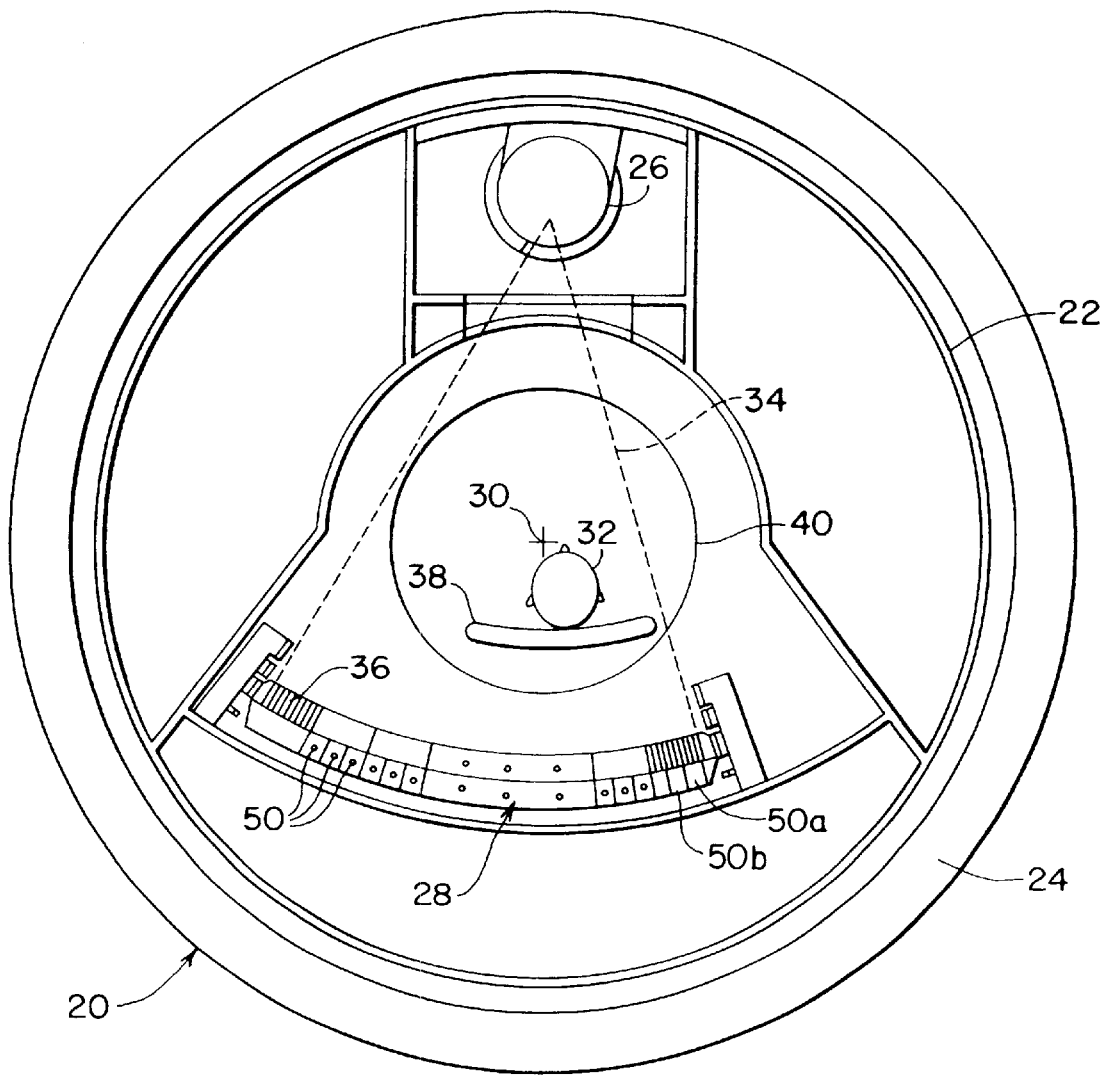
FIG. 1 is a simplified end view of a third generation filtered CT scanner including a monitor detector assembly provided in accordance with the present invention.
Figure 2:
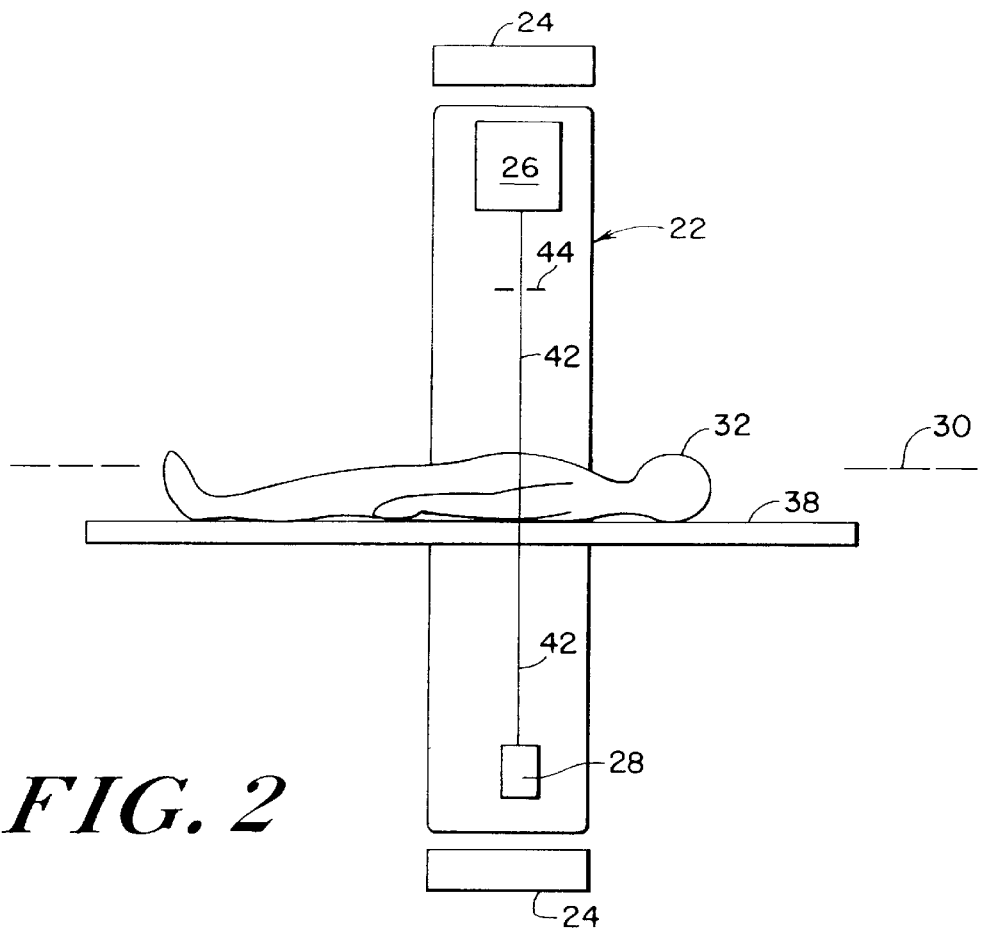
FIG. 2 is a simplified radial view of the filtered CT scanner shown in FIG. 1.

Referring to the drawings for a more complete understanding of the present invention, FIGS. 1 and 2 represent a CT scanner 20 of the third generation type modified to incorporate the present invention. The system depicted in FIGS. 1 and 2 comprises a disk 22 mounted for rotation in a stationary gantry support 24. The disk 22 supports an X-ray source 26 and an arcuate image data detector array assembly 28 comprising a plurality of detectors 50. Source 26 and detector assembly 28 are rotated about rotation axis 30 (extending normal to the view shown in FIG. 1) so as to rotate around the object 32 that extends through the central opening of the disk during the CT scan. Object 32 may be a part of a live human patient, such as the head or torso, a phantom for calibrating the scanner, or some other object of interest. Source 28 emits radiation through a collimator 44 (shown in FIG. 2) so as to define within a scanning plane (normal to rotation axis 30 and shown at 42 in FIG. 2), a continuous fan-shaped beam 34 of X-rays (seen in FIG. 1), which is sensed by the detectors of assembly 28 after passing through object 32. Object 32 may be supported, for example, on a pallet or table 38, which of course, should be as transparent as practical to X-rays. As disk 22 rotates, detectors 50 of assembly 28 are periodically sampled, in a predetermined sequence to provide discrete measurements of X-rays passing in the scanning plane through object 32 from many projection angles. The measurements are then processed electronically with appropriate signal processing equipment (described hereinafter, by way of example, in connection with FIG. 3), in accordance with any well-known mathematical and processing techniques, so as to produce the final image information. The image information may then be placed in memory, analyzed in a computer, or suitably displayed. The final image will be one of the mass contained within the "field of view" of the scanner (as indicated by the circle 40 in FIG. 1) within the scanning plane (shown at 42 in FIG. 2). At least one, and preferably two of the detectors 50, indicated at 50a and 50b, are used as monitor detectors (and therefore designated hereinafter as the "monitor" detectors) for monitoring the values of the level of X-rays received by the monitor detectors during each view of the CT scan. In the embodiment shown, the two monitor detectors form the two end detectors of the asymmetric end of the arcuate detector array 28. Alternatively, a single monitor detector can be used, or the arcuate detector array can be symmetrical, and/or the monitor detectors can be any two detectors, for example, the detectors respectively at the opposite ends of the array 28.

Figure 3:
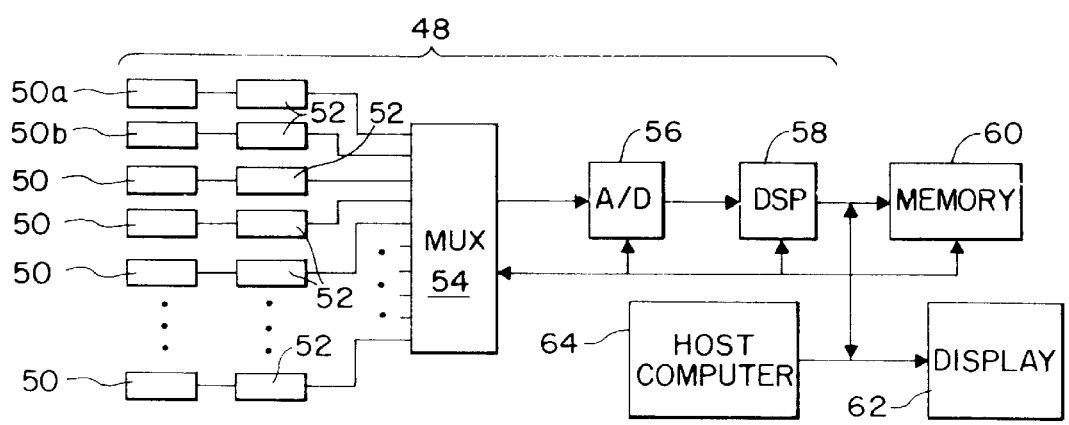
FIG. 3 is a block diagram of the image data detectors and the supporting electronics for the arcuate image detector array of FIGS. 1 and 2.

As shown in FIG. 3, each data detector 50 of detector array assembly 28, forms a part of the data acquisition system (DAS), generally indicated at 48. The DAS 48 further includes a preamplifier, low-pass filter and integrator 52 for amplifying, filtering and integrating the output of each detector for each projection. The output of each preamplifier, low pass filter and integrator 52 is connected to a multiplexer 54 of the DAS 48 for sequentially applying the signal outputs of the preamplifier, filter and integrator 52 to the input of an analog to digital (A/D) converter 56 of the DAS 48 for converting the analog signals to digital signals representative of the analog signals. The digital signal output of the A/D converter 56 is applied to a digital signal processor 58 of the DAS which stores the data in memory 60. The processor 58 includes a central processing unit (CPU) for controlling the operation of the components of the DAS 48, including the integration cycles of the preamplifier, low pass filter and integrator 52, in a manner which is well known. Memory 60 is large enough to store at least one complete set of data for an entire scan. The data can be retrieved and an image reconstructed and displayed on a display 62 in a manner which is well known. In this regard the memory preferably is also connected to a host computer 64, preferably provided with an array processor for reconstructing the image, and connected to display 62 for displaying the reconstructed image. In this case all of the detectors are connected to one multiplexer. It should be appreciated that the detectors can be divided into two or more groups, with the detectors of each group connected to its own multiplexer and A/D converter, and subsequently processed and stored. This increases the speed of operation at the expense of additional hardware.

When performing a scan it should be evident that during certain views the object 32 or table 38 could partially obstruct the rays from the X-ray source 26 and the one or both of the monitor detectors 50a and 50b. In the preferred embodiment shown, the monitor readings, in counts, are the sum of the offset-corrected readings from the two monitor detectors 50a and 50b. In accordance with one aspect of the invention, an improved method of and system for correcting for X-ray fluctuations is provided which adapts so as to correct of those monitor readings in which the X-rays received by the monitor detectors 50a and 50b are obstructed by the object 30 or table 38, or other object that may get in the way. The adaptive monitor correction method and system uses all monitor readings for a scan to find views where monitor detectors are obstructed. Reference readings for obstructed views are replaced with one or more values calculated based on the remaining valid monitor readings. The values for the obstructed views are preferably statistically determined.

Statistical analysis of all monitor readings for a scan is used to find obstructed monitor views. In the preferred embodiment, monitor readings, in counts, are the sum of the offset-corrected readings from the two monitor detectors. At least one value of the level of X-rays received during each view is used, although multiple readings at respectively different times of a view can be used, as is suggested, for example, in the '427 Patent. Preferably, the histogram of the values of all input monitor readings is computed. The histogram peak value and the corresponding bin number are found. The closest bin with the histogram value below a preset fraction of the peak value is found on both sides of the peak bin location (upper and lower cutoff bins). The upper and lower cutoff levels are calculated as monitor readings corresponding to the centers of the cutoff bins.

The value below which the monitor is considered to be obstructed is set at the lower cutoff level. To find regions where one or both of the monitor detectors 50a and 50b are obstructed, monitor readings are first low-pass filtered. The average of filtered monitor readings between the lower and upper cutoff levels is used as the obstructed monitor replacement value. Obstructed monitor regions are defined as regions where filtered monitor readings are below the lower cutoff level, plus adjacent "shoulder" areas where filtered monitor readings increase from the lower cutoff level to the replacement value. The lower cutoff level is chosen so as to provide a threshold value which is below the range of the low-pass filtered monitor data in the unobstructed region. The width of the low-pass filter is chosen to cover the temporal extent of typical x-ray output fluctuations, such as those induced by the anode rotation. It is also chosen to be narrower than the temporal extent of a typical obstructed monitor region. Therefore, views where filtered monitor readings are below the lower cutoff level are well inside the obstructed region. The "shoulder" areas are added to find views where monitor detectors are likely to be obstructed, even though filtered monitor readings are above the threshold. The upper cutoff level is chosen to prevent spikes in the X-ray flux from affecting the monitor replacement value.

The following is a summary of the algorithm using examples of typical values and used to determine the obstructed views and provide substitute values so that the can be used to normalize the CT data acquired during a scan. It should be appreciated that the values given can vary depending on the construction and operation of the scanner.

1.1 Input
M(v) Sum of the two monitor detector readings in counts
$0 \leq v < N_v$ 1.2 Output
$M_{amc}(v)$ Corrected monitor readings in counts, $0 \leq v < N_v$ 1.3 Parameters

| | |
|---|---|
| $N_v$ | Number of views, |
| | 1440 for axial scans, $\geq$ 2880 for spiral scans |
| $N_b = 1000$ | Number of histogram bins |
| $N_f = 4$ | Width of the boxcar filter is $2N_f + 1$ |
| $\varepsilon_{amc} = 0.1$ | Relative monitor threshold in histogram |

Figure 4:
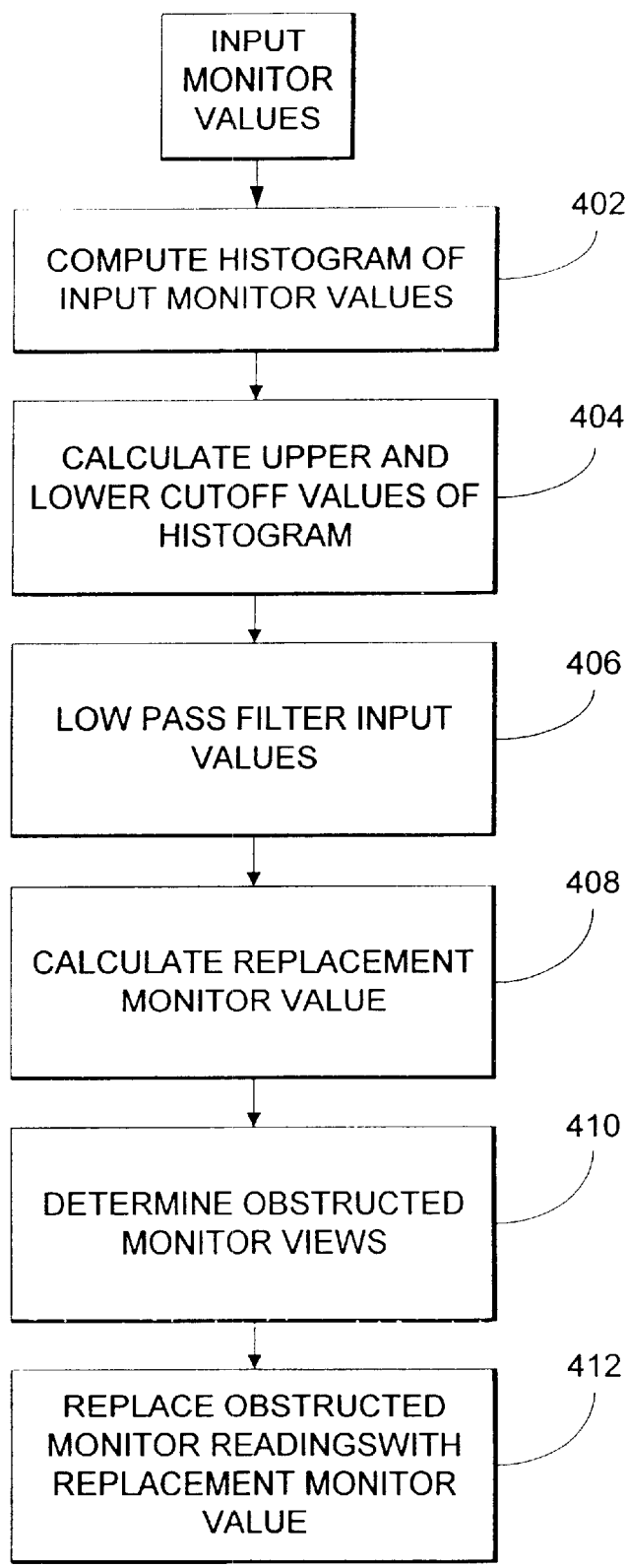
FIG. 4 is a flow chart illustrating the preferred detailed embodiment of the method of the present invention.

1.4 Description of the Method
Referring to flow chart of FIG. 4,
1. As shown at step 402, compute the histogram of the input monitor values. The bin width of the histogram, $W_b$, is set based on the highest monitor value:

$$W_b = \frac{\max M(v)}{N_b - 1} \quad (1)$$

The histogram H(i), $0 \leq i < N_b$, is then defined as $$H(i) = \text{number of input views } v \text{ for which } iW_b \leq M(v) < (i+1)W_b \quad (2)$$

The use of $N_b-1$ in the denominator in Equation 1 ensures that the last histogram bin is empty.

2. At step 404, calculate the upper and lower cutoff levels from the histogram.

(a) Find the location of histogram peak, $i_{max}$, $$i_{max}=n, \ H(n)=\max H(i) \quad (3)$$

(b) Find the highest bin number below the $i_{max}$, (walking away from the peak location) where the histogram value is less than the fraction of peak value given by the parameter $\epsilon_{amc}$, $$i_{tml} = \max_{n<i_{max}} n, \ H(n) \leq \varepsilon_{amc} \max_i H(i) \quad (4)$$

The lower cutoff level in counts, $M_l$, is then given by the bin center $$M_l = \left(i_{tml} + \frac{1}{2}\right) W_b \quad (5)$$

(d) Find the lowest bin number above the $i_{max}$ (walking away from the peak location) where the histogram value is less than the fraction of peak value given by the parameter $\epsilon_{amc}$, $$i_{tmu} = \min_{n>i_{max}} n, \ H(n) \leq \varepsilon_{amc} \max_i H(i) \quad (6)$$

The value of $i_{tmu}$ is always defined because the last bin of the histogram is always empty.

(e) The upper cutoff level in counts, $M_u$, is then given by the bin center $$M_u = \left(i_{tmu} + \frac{1}{2}\right) W_b \quad (7)$$

3. At step 406, low-pass filter the input data. Filtered monitor readings, $M_f(v)$, are calculated using sliding average:

$$M_f(v) = \begin{cases} \frac{1}{2N_f+1} \sum_{n=-N_f}^{N_f} M(v+n) & N_f \leq v < N_v - N_f \\ M_f(N_f) & 0 \leq v < N_f \\ M_f(N_v - N_f - 1) & N_v - N_f \leq v < N_v \end{cases} \quad (8)$$

4. At step 408, calculate the replacement monitor value, $M_r$, defined as averaged filtered monitor values $M_f(v)$ that are between the lower and upper monitor thresholds $M_l$ and $M_u$, $$M_r = \overline{M_f(v)}, \ M_l < M_f(v) < M_u \quad (9)$$

5. At step 410, find views where the monitor is obstructed. The monitor is considered obstructed in the following regions:

(a) all of the views v for which the filtered monitor value $M_f(v)$ is below the obstructed monitor threshold $M_l$, (b) the "shoulder" regions—contiguous sets of views v adjacent to regions marked in step 5a for which the filtered monitor value $M_f(v)$ is below the replacement monitor value $M_r$, 6. At step 412, replace obstructed monitor readings with the replacement monitor value $M_r$. Corrected monitor readings are then given by $$M_{amc}(v) = \begin{cases} M_r & \text{view } v \text{ had obstructed monitor per step 5} \\ M(v) & \text{otherwise} \end{cases} \quad (10)$$

It should be appreciated that the foregoing algorithm can be applied to the complete set of views in both axial and helical modes of operation, i.e., during a constant axis scan or a helical scan. Further, the adaptive monitor correction can be run simultaneously with the reconstruction algorithm for generating a CT image from the CT data provided, or alternatively, as a preprocessing step before going through the rest of the reconstruction algorithm.

The entire algorithm can be carried out in software on the host computer 64.

The monitor values obtained are thus used to account for fluctuations in the incident X-ray intensity during the air scan and the object scan. Unobstructed views provide the air scan data for normalizing the CT data acquired during each view. If a monitor detector is obstructed, the monitor data no longer reflects the incident X-ray intensity, which can lead to image artifacts. The algorithm statistically analyzes the monitor data, identifies readings where the monitor detector was obstructed, and replaces obstructed monitor readings with a value consistent with unobstructed monitor readings for the scan. The resulting set of values are then used to normalize the corresponding CT data acquired during the same scan.

Figure 5:
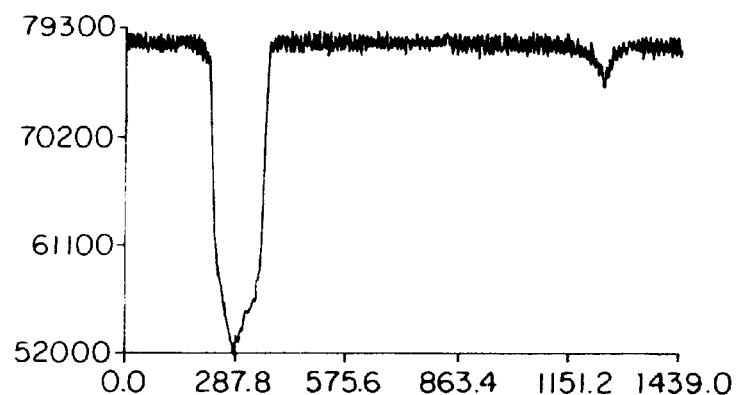
FIG. 5 illustrates an example of raw monitor data in counts with two groups of monitor obstructed views.

FIG. 5 illustrate an example of raw monitor data, before correction, in counts with two groups of monitor obstructed views. The monitor detectors were obscured by a patient table during two parts of the scan. Monitor data represent the sum of the two monitor detector readings in counts.

Figure 6:
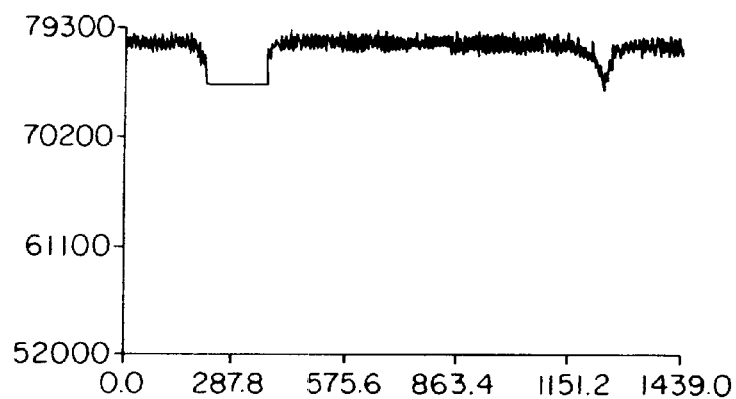
FIG. 6 shows the results of a thresholded monitor correction, prior art method.
Figure 11:
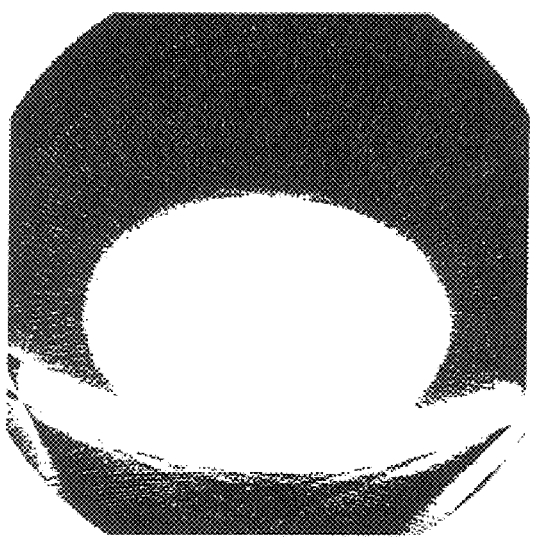
FIG. 11 shows a reconstructed image having visible artifacts using the thresholded monitor values.

The current version of one commercially available scanner image reconstruction algorithm uses a threshold to find obstructed monitor values and replaces them with the previous non-obstructed monitor value. The threshold is set at 95 percent of the average air monitor value which is included in the air table. The threshold was set to be lower than the typical range of monitor reading fluctuations due to noise and anode wobble in order to avoid cutting off the lowest of the valid monitor values. The prior art algorithm is suitable for pipeline implementation, since it only uses one input view at a time. Results of the thresholded monitor correction are shown in FIG. 6. Only one region of monitor obstructed views is corrected. Monitor readings are allowed to drop well below the average for the scan before being replaced. The replacement monitor value is also well below the average monitor reading for the scan. Reconstructing an image using the thresholded monitor values results in the artifact visible in the image in FIG. 11.

Figure 7:
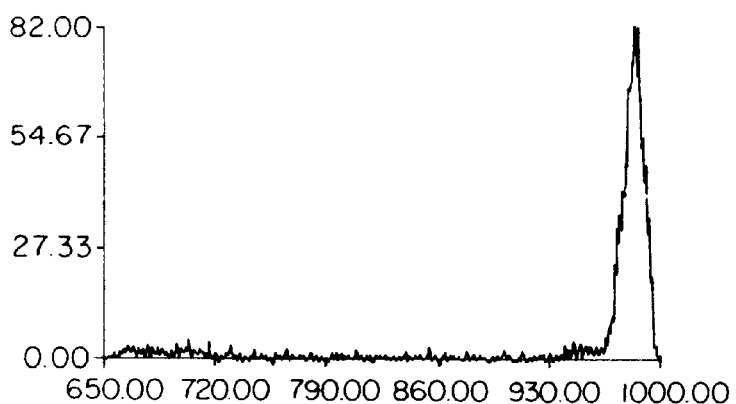
FIG. 7 shows a histogram of input monitor values, which is used to automatically set the obstructed monitor threshold.
Figure 8:
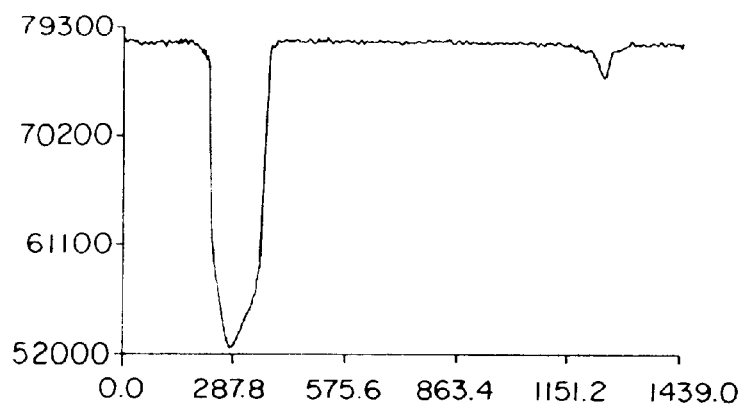
FIG. 8 shows the low-pass filtered monitor values, which are used to set the monitor replacement value and to find the views where monitor is obstructed.
Figure 9:
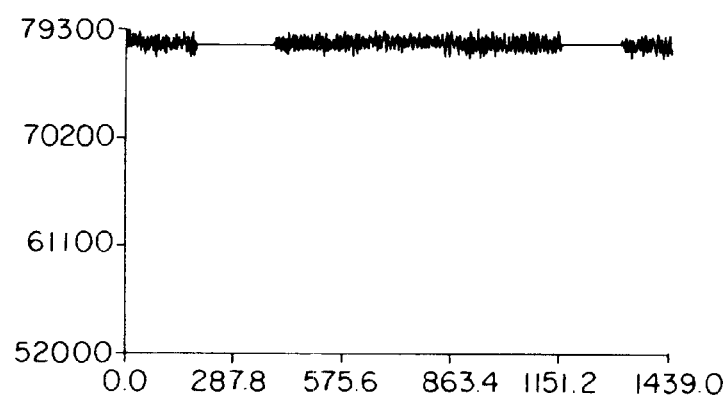
FIGS. 9 and 10 show corrected monitor values.
Figure 10:
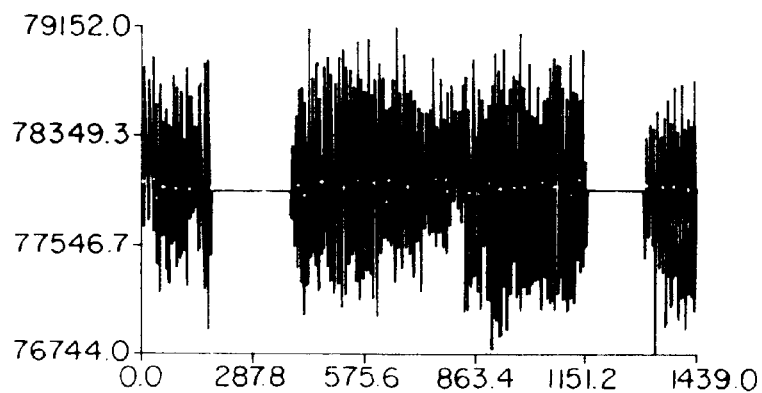
Figure 12:
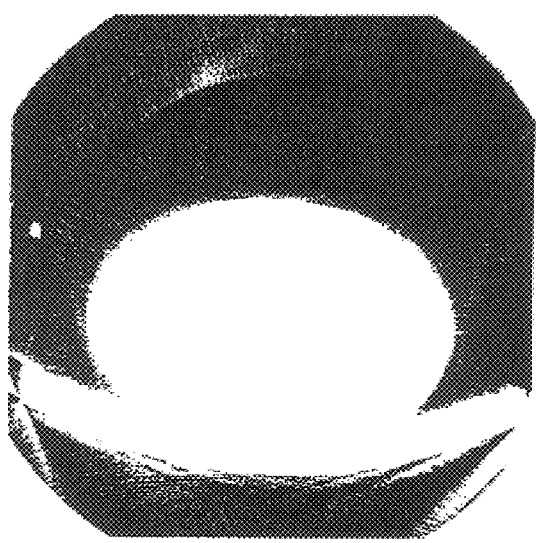
FIG. 12 shows an image reconstructed with the adaptive monitor correction of the present invention.

The adaptive monitor correction algorithm of the present invention improves upon the thresholded monitor correction of the prior art by analyzing a complete set of views for a scan. Data for all views are available where the scanner performs online reconstruction without the use of a pipeline architecture. Statistical analysis of all monitor values for a scan allows the adaptive monitor correction algorithm to find both regions where monitor detectors were obstructed and to find the monitor replacement value which is consistent with unobstructed monitor readings. The histogram of input monitor values, which is used to automatically set the obstructed monitor threshold, is shown in FIG. 7. The low-pass filtered monitor values, which are used to set the monitor replacement value and to find the views where monitor is obstructed, is shown in FIG. 8. The corrected monitor values are shown in FIGS. 9 and 10. Both regions where monitor detectors were obstructed have been corrected, and the monitor replacement value is in the middle of the unobstructed monitor range. The image reconstructed with adaptive monitor correction is shown in FIG. 12. The artifact in the upper portion of the image is removed.

In summary, the adaptive monitor correction algorithm reduces image artifacts by finding the views where monitor detectors are obstructed and replacing monitor readings for those views with an average value. The statistical nature of the algorithm allows it to adapt to changes in both the amplitude and the noise level of monitor data. However, the algorithm requires access to full monitor data for a scan.

While the preferred embodiment has been described as a third generation CT scanner, the invention can be employed in other types of multiple exposure imaging systems, including fourth generation CT scanners.

Other modifications and implementations will occur to those skilled in the art without departing from the spirit and the scope of the invention as claimed. Accordingly, the above description is not intended to limit the invention except as indicated in the following claims.

What is claimed:

1. A system for performing CT scans, comprising:
    an X-ray source for providing X-rays during a plurality of views of a CT scan;
    a subsystem for correcting for X-ray fluctuations occurring during a CT scan, including:
        measurement means for measuring at least one value of the level of X-rays received from the X-ray source during each view;
        determination means for determining which of the measured values of levels of X-rays represent at least partially attenuated measurements due to an unintended obstruction during the measurement; and
        replacement means for replacing measured values of levels of X-rays representing partially attenuated measurements with replacement values determined from values of remaining measurements.

2. A system according to claim 1, wherein the subsystem further includes:
    normalization means for using the replacement values and remaining values to normalize CT data acquired during the CT scan.

3. A system according to claim 1, further comprising:
    a detector array; and
    means rotating the X-ray source and detector array so as to generate CT data representing multiple views of an object positioned between the X-ray source and detector array during a CT scan.

4. A system according to claim 1, wherein the determination means includes statistical determination means for statistically determining the measured values of levels of X-rays representing partially attenuated measurements.

5. A system according to claim 1, wherein the determination means includes means for determining a histogram of all of the measured values of X-rays during a scan.

6. A system according to claim 5, wherein the determination means includes means for determining the upper and lower cutoff values of the histogram.

7. A system according to claim 6, wherein the determination means further includes means for low pass filtering all of the measured values of X-rays during a scan.

8. A system according to claim 7, wherein the replacement means for replacing measured values of levels of X-rays representing partially attenuated measurements with replacement values determined from values of remaining measurements includes means for determining an averaged filtered monitor value that are between the lower and upper monitor cutoff values of the histogram.

9. A system according to claim 8, wherein the determination means for determining which of the measured values of levels of X-rays represent at least partially attenuated measurements due to an unintended obstruction during the measurement includes means for establishing which of the filtered monitor values is below the lower monitor cutoff value of the histogram.

10. A system according to claim 9, wherein the determination means for determining which of the measured values of levels of X-rays represent at least partially attenuated measurements due to an unintended obstruction during the measurement further includes means for determining contiguous sets of views in which the filtered monitored value is below the monitor replacement value, and that are adjacent to the views in which the filtered monitor value is below the lower monitor cutoff value, and establishing such contiguous sets of views as attenuated measurements.

11. A method of normalizing CT data acquired exposing an object with X-rays from a X-ray source through multiple views using a detector monitor subassembly, comprising:
    measuring at least one value of the level of X-rays received from the X-ray source during each view;
    determining which of the measured values of levels of X-rays represent at least partially attenuated measurements due to an unintended obstruction during the measurement; and
    replacing measured values of levels of X-rays representing partially attenuated measurements with replacement values determined from values of remaining measurements.

12. A method according to claim 11, further including:
    using the replacement values and remaining values to normalize CT data acquired during the CT scan.

13. A method according to claim 11, wherein determining which of the measured values of levels of X-rays represent at least partially attenuated measurements due to an unintended obstruction during the measurement includes statistically determining the measured values of levels of X-rays representing partially attenuated measurements.

14. A method according to claim 13, wherein determining which of the measured values of levels of X-rays represent at least partially attenuated measurements due to an unintended obstruction during the measurement includes determining a histogram of values of all of the measured values of X-rays during a scan.

15. A method according to claim 14, wherein determining which of the measured values of levels of X-rays represent at least partially attenuated measurements due to an unintended obstruction during the measurement further includes determining the upper and lower cutoff values of the histogram.

16. A method according to claim 15, wherein determining which of the measured values of levels of X-rays represent at least partially attenuated measurements due to an unintended obstruction during the measurement further includes low pass filtering all of the measured values of X-rays during a scan.

17. A method according to claim 16, wherein replacing measured values of levels of X-rays representing partially attenuated measurements with replacement values determined from values of remaining measurements includes means for determining an averaged filtered monitor value that is between the lower and upper monitor cutoff values of the histogram.

18. A method according to claim 17, wherein the determination means for determining which of the measured values of levels of X-rays represent at least partially attenuated measurements due to an unintended obstruction during the measurement includes establishing which of the filtered monitor values is below the lower monitor cutoff value of the histogram.

19. A method according to claim 18, wherein determining which of the measured values of levels of X-rays represent at least partially attenuated measurements due to an unintended obstruction during the measurement further includes determining contiguous sets of views in which the filtered monitor value is below the monitor replacement value, and that are adjacent to the views in which the filtered monitor value is below the lower monitor cutoff value, and establishing such contiguous sets of views as attenuated measurements.

* * * * *